(12) United States Patent
Brown

(10) Patent No.: US 8,981,286 B2
(45) Date of Patent: Mar. 17, 2015

(54) MASS SPECTROMETER INCORPORATING HYDROGEN-DEUTERIUM EXCHANGE

(75) Inventor: Jeffery Mark Brown, Hyde (GB)

(73) Assignee: Micromass UK Limited, Wilmslow (GB)

( * ) Notice: Subject to any disclaimer, the term of this patent is extended or adjusted under 35 U.S.C. 154(b) by 61 days.

(21) Appl. No.: 13/578,397

(22) PCT Filed: Feb. 14, 2011

(86) PCT No.: PCT/GB2011/050273
§ 371 (c)(1),
(2), (4) Date: Dec. 14, 2012

(87) PCT Pub. No.: WO2011/098833
PCT Pub. Date: Aug. 18, 2011

(65) Prior Publication Data
US 2013/0206974 A1    Aug. 15, 2013

Related U.S. Application Data

(60) Provisional application No. 61/307,882, filed on Feb. 25, 2010.

(30) Foreign Application Priority Data

Feb. 12, 2010    (GB) .................................. 1002445.3

(51) Int. Cl.
*H01J 49/00*    (2006.01)
*H01J 49/02*    (2006.01)
*G01N 27/62*    (2006.01)

(52) U.S. Cl.
CPC ......... *H01J 49/0031* (2013.01); *H01J 49/0077* (2013.01); *H01J 49/02* (2013.01); *G01N 27/622* (2013.01)
USPC ............................ 250/282; 250/288; 250/281

(58) Field of Classification Search
USPC ....................................................... 250/282
See application file for complete search history.

(56) References Cited

U.S. PATENT DOCUMENTS

| 6,570,155 B1 * | 5/2003 | Prior et al. ................ 250/311 |
| 6,703,609 B2 * | 3/2004 | Guevremont et al. ........ 250/287 |
| 6,906,320 B2 * | 6/2005 | Sachs et al. .................... 250/282 |
| 6,982,414 B2 * | 1/2006 | Bateman et al. ............... 250/282 |
| 7,586,088 B2 * | 9/2009 | Bateman et al. ............... 250/281 |
| 2003/0038235 A1 | 2/2003 | Guevremont et al. |
| 2004/0181351 A1 * | 9/2004 | Thompson et al. ............. 702/76 |
| 2006/0289747 A1 | 12/2006 | Schultz et al. |
| 2011/0114835 A1 | 5/2011 | Chen et al. |

FOREIGN PATENT DOCUMENTS

| WO | 2009/064350 | 5/2009 |
| WO | 2010/120895 | 10/2010 |

OTHER PUBLICATIONS

Purves, et. al., "Combining H—D exchange and ESI-FAIMS-MS for detecting gas-phase conformers of equine cytochrome c1", Can. J. Chem. 83; pp. 1961-1968 (2005).*
Valentine and Clemmer, "H/D Exchange Levels of Shape-Resolved Cytochrome c Conformers in the Gas Phase", J. Am. Chem. Soc. 1997, 119, 3558-3566.*
Valentine, "H/D Exchange Levels of Shape-Resolved Cytochrome c Conformers in the Gas Phase", J.Am. Chem. Soc. 1997, 119, 3558-3566.*
Kasper D. Rand et al. "Gas-Phase Hydrogen/Deuterium Exchange in a Traveling Wave Ion Guide for the Examination of Protein Conformations", *Analytical Chemistry*, vol. 81, No. 24, pp. 10019-10028, Dec. 15, 2009.
Robinson et al. "Multidimensional Separations of Ubiquitin Conformers in the Gas Phase: Relating Ion Cross Sections to H/D Exchange Measurements", *Journal of the American Society for Mass Spectrometry*, vol. 16, No. 9, pp. 1427-1437, Sep. 1, 2005.
Valentine et al. "H/D Exchange Levels of Shape-Resolved Cytochrome c Conformers in the Gas Phase", *Journal of American Chemical Society*, vol. 119, No. 15, pp. 3558-3566, Apr. 1, 1997.
Kornel Nagy et al. "Online Hydrogen/Deuterium Exchange Performed in the Ion Mobility Cell of a Hybrid Mass Spectrometer", *Analytical Chemistry*, vol. 81, No. 22, pp. 9365-9371, Nov. 15, 2009.
Randy Purves et al. "Combining H-D) Exchange and ESI-FAIMS-MS for Detecting Gas-Phase Conformers of Equine Cytochrome c", *Canadian Journal of Chemistry*, vol. 83, pp. 1961-1968, Jan. 27, 2006.

* cited by examiner

*Primary Examiner* — Phillip A Johnston
(74) *Attorney, Agent, or Firm* — Diederiks & Whitelaw, PLC

(57) ABSTRACT

A mass spectrometer is disclosed comprising a hydrogen-deuterium exchange cell. Isomeric ions having different conformations but substantially similar ion mobilities can be differentiated by subjecting the ions to hydrogen-deuterium exchange. Two ions having similar ion mobilities can be differentiated more effectively if they have different surface conformations by determining the relative degree of hydrogen-deuterium exchange.

13 Claims, 4 Drawing Sheets

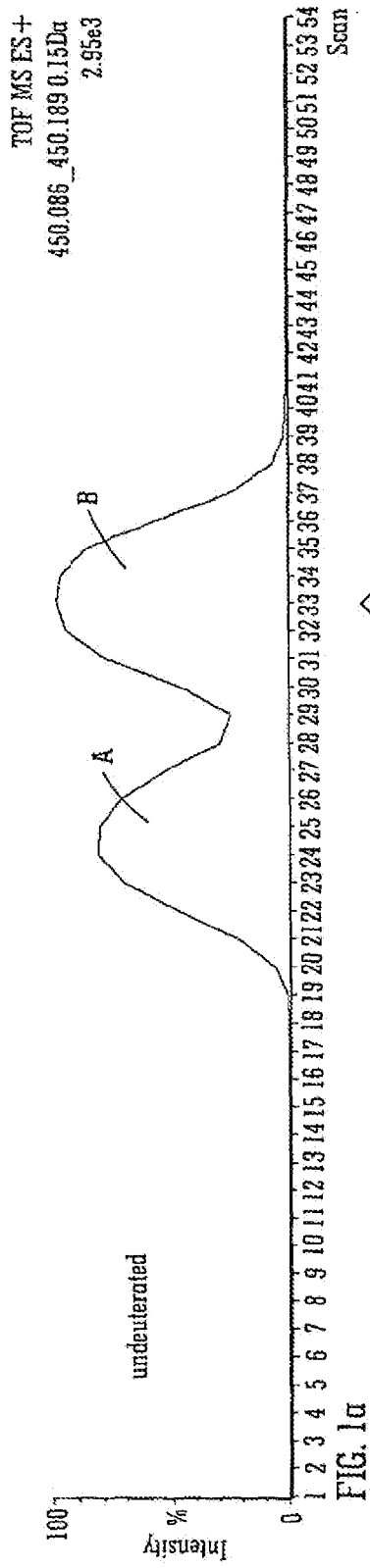
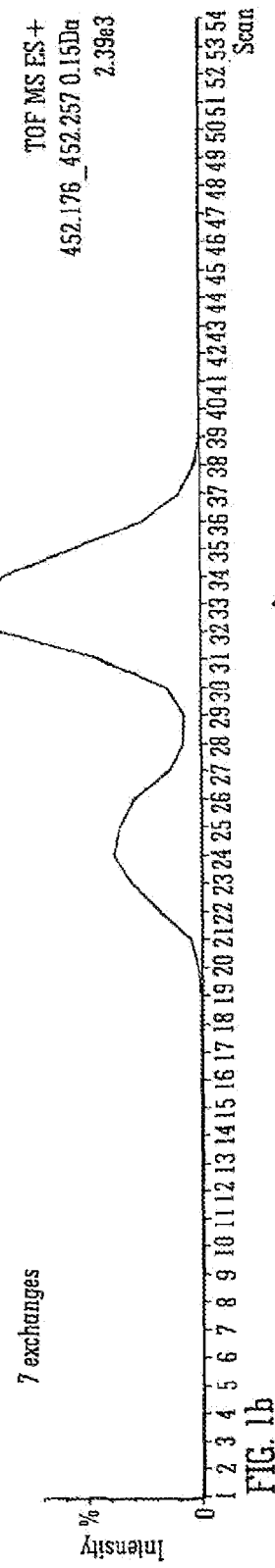
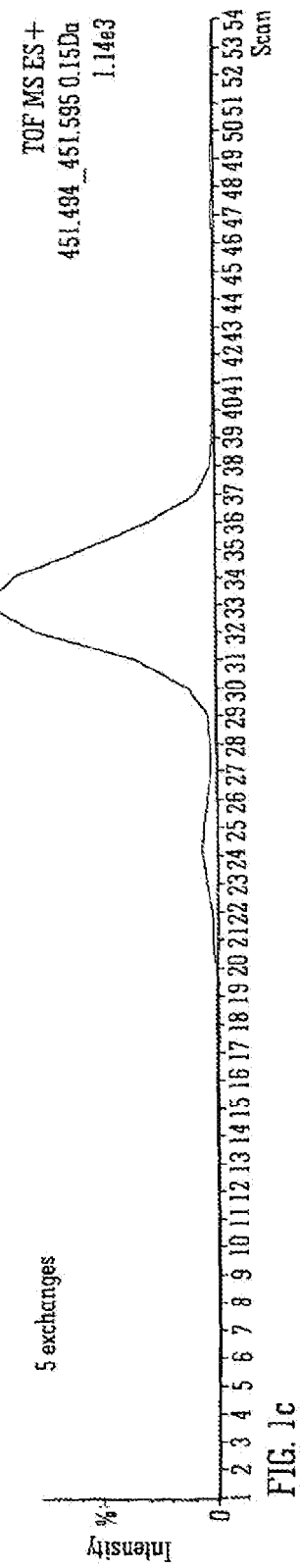

FIG. 2a undeuterated Drift = 34 channels TOF MS ES+ 518

FIG. 2b undeuterated Drift = 24 channels TOF MS ES+ 1.17e3

FIG. 2c with HDX Drift = 24 channels TOF MS ES+ 573

FIG. 2d with HDX Drift = 34 channels TOF MS ES+ 1.13e3

FIG. 2e Simulated HDX with 5 exchanges TOF MS ES+ 4.24e12

FIG. 2f Simulated HDX with 7 exchanges TOF MS ES+ 4.24e12

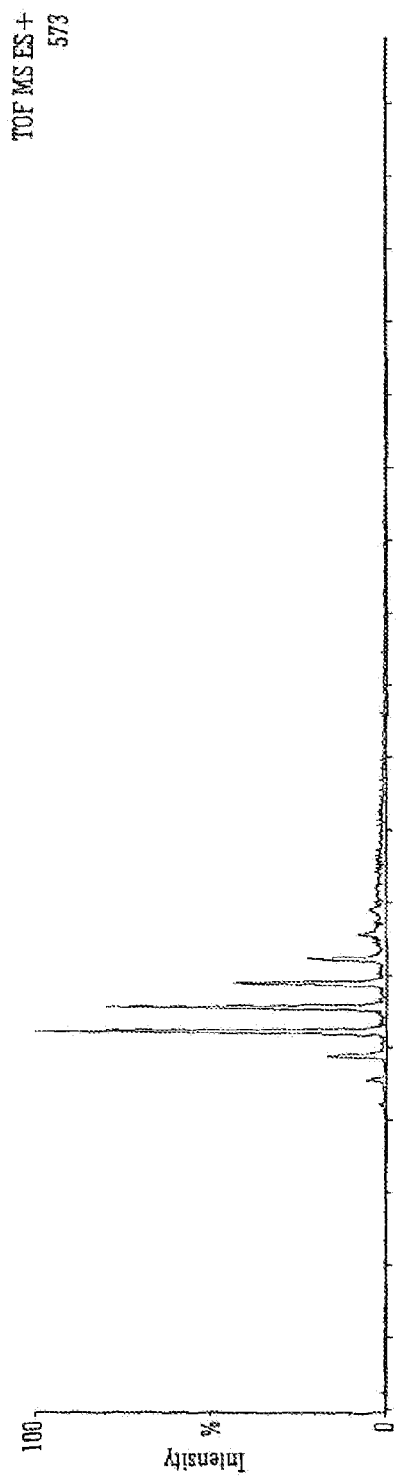
FIG. 3α
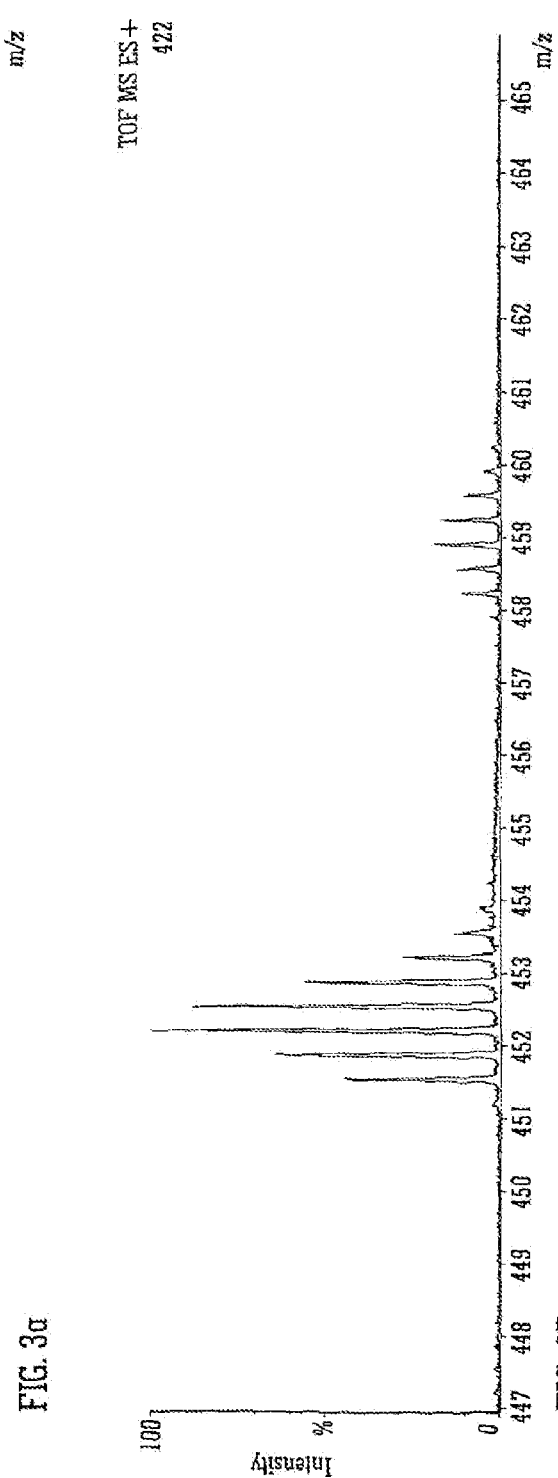
FIG. 3B

MASS SPECTROMETER INCORPORATING HYDROGEN-DEUTERIUM EXCHANGE

CROSS-REFERENCE TO RELATED APPLICATIONS

This application represents a National Stage application of PCT/GB2011/050273 entitled "Mass Spectrometer Incorporating Hydrogen-Deuterium Exchange" filed 14 Feb. 2011 which claims priority from and the benefit of U.S. Provisional Patent Application Ser. No. 61/307,880 filed on 25 Feb. 2010 and United Kingdom Patent Application No. 1002447.9 filed on 12 Feb. 2010. The entire contents of these applications are incorporated herein by reference.

BACKGROUND TO THE INVENTION

The present invention relates to a method of mass spectrometry and a mass spectrometer.

It is known to separate ions according to their ion mobility in an ion mobility spectrometer.

A mass filter may be provided upstream of an on mobility spectrometer and may be set to transmit only ions having a certain mass to charge ratio. In some circumstances two ions having slightly different ion mobilities can be partially resolved by the ion mobility spectrometer suggesting that the ions comprise two isomers having, different conformations and with the difference in ion mobility being due to the different conformations. However, conventional ion mobility separation techniques provide limited information about the different conformations and it may be desired to have both a greater degree of understanding concerning the nature of the two different conformations and also a greater degree of confidence that the observed ion peaks in an ion chromatogram do in fact represent ions having different conformations.

In other circumstances the ion mobility spectrometer may be unable to resolve ions having different conformations so that a single ion peak is observed in a resulting ion chromatogram. However, it may be desired to see whether a single ion peak in an ion chromatogram actually comprises two (or more) isomers having different conformations.

Conventional ion mobility spectrometry techniques provide only a limited amount of information and a limited degree of certainty when seeking to analyse isomeric ions.

It is desired to provide an improved method of mass spectrometry and mass spectrometer.

SUMMARY OF THE INVENTION

According to an aspect of the present invention there is provided a method of mass spectrometry comprising:

subjecting first and second analyte ions to hydrogen-deuterium exchange within a first device wherein one or more hydrogen atoms of the first and second analyte ions exchange with one or more deuterium atoms to form first and second deuterated ions;

passing the first and second deuterated ions from the first device to an ion mobility spectrometer;

mass analysing deuterated ions which emerge from the ion mobility spectrometer at a first time to produce first mass spectral data;

mass analysing deuterated ions which emerge from the ion mobility spectrometer at a second later time to produce second mass spectral data; and comparing the first mass spectral data with the second mass spectral data to aid differentiation between either: (i) the first and second acolyte ions; and/or (ii) the first deuterated ions and the second deuterated ions.

The preferred embodiment relates to a method wherein ions are subjected to hydrogen-deuterium exchange ("HDX") by, for example, passing the ions through a gas cell containing deuterated ammonia gas. One of more hydrogen atoms in the analyte ions are exchanged for deuterium which results in an increase in the resulting mass to charge ratio of the ions. The deuterated ions may then be passed to an ion mobility separator or spectrometer wherein the ions may be partially separated temporally or partially resolved by virtue of having slightly different drift times through the ion mobility separator or spectrometer on account of having different conformations (i.e. structural arrangements). For example, ions having a compact structure may emerge from the ion mobility spectrometer prior to ions having a more elongated structure. An ion may give rise to an isotope pattern in a final mass spectrum. The isotope pattern can be analysed or deconvoluted to determine the relative number of hydrogen atoms which have been exchanged for deuterium. As a result, further information concerning the conformational properties of two ions having similar or identical masses can be determined and a greater degree of confidence can be obtained that two ions which are believed to be isomeric ions having different conformations do in fact have different conformations. Other embodiments are contemplated wherein the ions may first be passed through an ion mobility spectrometer before then passing to a gas cell where the ions are subjected to hydrogen-deuterium exchange.

Hydrogen-deuterium exchange probes the surface of an ion and ion mobility spectrometry differentiates ions on the basis of cross-section. These two parameters are linked in that if the cross-section is different then it is highly likely the surface conformation is also different and vice versa.

The step of passing the first and second deuterated ions from the first device to the ion mobility spectrometer preferably further comprises temporally separating the first and second deuterated ions within the ion mobility spectrometer.

According to an aspect of the present invention there is provided a method of mass spectrometry comprising:

passing first and second analyte ions to an ion mobility spectrometer;

subjecting the first and second analyte ions which emerge from the ion mobility spectrometer to hydrogen-deuterium exchange within a first device wherein one or more hydrogen atoms of the first and second analyte ions exchange with one or more deuterium atoms to form first and second deuterated ions;

mass analysing deuterated ions which emerge from the first device at a first time to produce first mass spectral data;

mass analysing deuterated ions which emerge from the first device at a second later time to produce second mass spectral data; and comparing the first mass spectral data with the second mass spectral data to aid differentiation between either: (i) the first and second analyte ions; and/or (ii) the first deuterated ions and the second deuterated ions.

The step of passing the first and second analyte ions to the ion mobility spectrometer preferably further comprises temporally separating the first and second analyte ions within the ion mobility spectrometer.

The preferred embodiment relates to methods of improved differentiation and determination of ionic conformations by combining hydrogen-deuterium exchange reactions with ion mobility separation techniques.

The step of comparing the first mass spectral data with the second mass spectral data to aid differentiation preferably comprises determining differences in structural or conformational properties or reactiveness with a gas in the first device between either: (i) the first and second analyte ions; and/or (ii) the first deuterated ions and the second deuterated ions.

The step of comparing the first mass spectral data with the second mass spectral data preferably comprises:

(i) determining or approximating the degree to which hydrogen atoms in the first and/or second analyte ions are exchanged for deuterium atoms; and/or (ii) determining or approximating structural or conformational properties of the first and/or second analyte ions; and/or (iii) determining or approximating structural or conformational properties of the first and/or second deuterated ions; and/or (iv) determining or approximating the relative compactness or elongation of the first and/or second analyte ions; and/or (v) determining or approximating the relative compactness or elongation of the first and/or second deuterated ions; and/or (vi) determining or approximating the degree to which the first and/or second analyte ions react with the gas in the first device to form adduct ions; and/or (vii) determining or approximating the number of surface sites on the first and/or second analyte ions at which hydrogen atoms may exchange for deuterium atoms; and/or (viii) comparing one or more isotope patterns and/or one or more isotope distributions and/or one or more isotope ratios related to the first deuterated ions with one or more isotope patterns and/or one or more isotope distributions and/or one or more isotope ratios related to the second deuterated ions.

The method preferably further comprises providing a mass filter upstream of the ion mobility spectrometer and/or the first device, and operating the mass filter to selectively transmit the first and second analyte ions having substantially the same mass to charge ratio and to filter out or attenuate other ions having different mass to charge ratios.

According to an aspect of the present invention there is provided a mass spectrometer comprising:

a first device arranged and adapted to subject first and second analyte ions to hydrogen-deuterium exchange wherein one or more hydrogen atoms of the first and second analyte ions exchange with one or more deuterium atoms to form first and second deuterated ions;

an ion mobility spectrometer, wherein the first and second deuterated ions are passed, in use, from the first device to the ion mobility spectrometer;

a mass analyser arranged and adapted to mass analyse deuterated ions which emerge from the ion mobility spectrometer at a first time to produce first mass spectral data and to mass analyse deuterated ions which emerge from the on mobility spectrometer at a second later time to produce second mass spectral data; and a control system arranged and adapted to compare the first mass spectral data with the second mass spectral data to aid differentiation between either: (i) the first and second analyte ions; and/or (ii) the first deuterated ions and the second deuterated ions.

According to an aspect of the present invention there is provided a mass spectrometer comprising:

an ion mobility spectrometer, wherein first and second analyte ions are passed to the ion mobility spectrometer;

a first device arranged and adapted to subject the first and second analyte ions which emerge from the ion mobility spectrometer to hydrogen-deuterium exchange within the first device wherein one or more hydrogen atoms of the first and second analyte ions exchange with one or more deuterium atoms to form first and second deuterated ions;

a mass analyser arranged and adapted to mass analyse deuterated ions which emerge from the first device at a first time to produce first mass spectral data and to mass analyse deuterated ions which emerge from the first device at a second later time to produce second mass spectral data; and a control system arranged and adapted to compare the first mass spectral data with the second mass spectral data to aid differentiation between either: (i) the first and second analyte ions; and/or (ii) the first deuterated ions and the second deuterated ions.

The control system is preferably arranged and adapted to determine differences in structural or conformational properties or reactiveness with a gas in the first device between either: (i) the first and second analyte ions; and/or (ii) the first deuterated ions and the second deuterated ions.

The control system is preferably arranged and adapted to:

(i) determine or approximate the degree to which hydrogen atoms in the first and/or second analyte ions are exchanged for deuterium atoms; and/or (ii) determine or approximate structural or conformational properties of the first and/or second analyte ions; and/or (iii) determine or approximate structural or conformational properties of the first and/or second deuterated ions; and/or (iv) determine or approximate the relative compactness or elongation of the first and/or second analyte ions; and/or (v) determine or approximate the relative compactness or elongation of the first and/or second deuterated ions; and/or (vi) determine or approximate the degree to which the first and/or second analyte ions react with the gas in the first device to form adduct ions; and/or (vii) determine or approximate the number of surface sites on the first and/or second analyte ions at which hydrogen atoms may exchange for deuterium atoms; and/or (viii) compare one or more isotope patterns and/or one or more isotope distributions and/or one or more isotope ratios related to the first deuterated ions with one or more isotope patterns and/or one or more isotope distributions and/or one or more isotope ratios related to the second deuterated ions.

The mass analyser preferably comprises a Time of Flight mass analyser.

The mass spectrometer preferably further comprises a mass filter arranged upstream of the ion mobility spectrometer and/or the first device, wherein in a mode of operation the mass filter is arranged and adapted to selectively transmit the first and second analyte ions having substantially the same mass to charge ratio and to filter out or attenuate other ions having different mass to charge ratios.

According to an aspect of the present invention there is provided a method of mass spectrometry comprising:

subjecting analyte ions to hydrogen-deuterium exchange within a first device wherein one or more hydrogen atoms of the analyte ions exchange with one or more deuterium atoms to form deuterated ions;

passing the deuterated ions from the first device to an ion mobility spectrometer;

mass analysing first deuterated ions which emerge from the ion mobility spectrometer at a first time to produce first mass spectral data;

deconvoluting one or more isotope ratio patterns in the first mass spectral data to determine or approximate the number of hydrogen atoms which have been exchanged for deuterium atoms in the first deuterated ions;

mass analysing second deuterated ions which emerge from the ion mobility spectrometer at a second later time to produce second mass spectral data; and deconvoluting one or more isotope ratio patterns in the second mass spectral data to determine or approximate the number of hydrogen atoms which have been exchanged for deuterium atoms in the second deuterated ions.

The method may further comprise comparing the number of hydrogen atoms which have been determined to have been exchanged for deuterium atoms on the first deuterated ions with the number of hydrogen atoms which have been determined to have been exchanged for deuterium atoms on the second deuterated ions.

According to an aspect of the present invention there is provided a mass spectrometer comprising:

a first device arranged and adapted to subject analyte ions to hydrogen-deuterium exchange wherein one or more hydrogen atoms of the analyte ions exchange with one or more deuterium atoms to form deuterated ions;

an ion mobility spectrometer, wherein the deuterated ions are passed, in use, from the first device to the ion mobility spectrometer;

a control system and mass analyser arranged and adapted:

(i) to mass analyse first deuterated ions which emerge from the ion mobility spectrometer at a first time to produce first mass spectral data;

(ii) to deconvolute one or more isotope ratio patterns in the first mass spectral data to determine or approximate the number of hydrogen atoms which have been exchanged for deuterium atoms in the first deuterated ions;

(iii) to mass analyse second deuterated ions which emerge from the on mobility spectrometer at a second later time to produce second mass spectral data; and (iv) to deconvolute one or more isotope ratio patterns in the second mass spectral data to determine or approximate the number of hydrogen atoms which have been exchanged for deuterium atoms in the second deuterated ions.

The control system may be arranged and adapted to compare the number of hydrogen atoms which have been determined to have been exchanged for deuterium atoms on the first deuterated ions with the number of hydrogen atoms which have been determined to have been exchanged for deuterium, atoms on the second deuterated ions.

According to an aspect of the present invention there is provided a method of mass spectrometry comprising:

subjecting analyte ions to hydrogen-deuterium exchange within a first device wherein one or more hydrogen atoms of the analyte ions exchange with one or more deuterium atoms to form deuterated ions;

mass analysing the deuterated ions to produce mass spectral data; and deconvoluting one or more isotope ratio patterns in the mass spectral data to determine or approximate the number of hydrogen atoms in the analyte ions which have been exchanged for deuterium atoms.

According to an aspect of the present invention there is provided a mass spectrometer comprising:

a first device arranged and adapted to subject analyte ions to hydrogen-deuterium exchange wherein one or more hydrogen atoms of the analyte ions exchange with one or more deuterium atoms to form deuterated ions;

a mass analyser arranged and adapted to mass analyse the deuterated ions to produce mass spectral data; and a control system arranged and adapted to deconvolute one or more isotope ratio patterns in the mass spectral data to determine or approximate the number of hydrogen atoms in the analyte ions which have been exchanged for deuterium atoms.

According to the preferred embodiment a method of significantly enhancing the differentiation of ionic conformations within a mass spectrometer equipped with an ion mobility drift cell device is provided. The preferred embodiment relates to improvements in the determination of ion mobility derived cross sectional areas by invoking hydrogen-deuterium exchange reactions. By measuring the differences in mass spectral modifications associated with hydrogen-deuterium exchange labelling either before or after an ion mobility device, ions with very similar cross-sections and identical mass to charge ratios can be differentiated and hence more accurately measured. Complementary methods are disclosed involving pattern matching of deuterated isotope clusters.

The preferred embodiment represents a significant improvement in the art.

According to an embodiment the mass spectrometer preferably further comprises:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") on source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source: (xix) an Atmospheric Sampling Glow Discharge Ionisation ("ASGDI") ion source; and (xx) a Glow Discharge ("GD") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable on reaction fragmentation device; (xxi) an ion-metastable molecule reaction fragmentation device (xxii) an ion-metastable atom reaction fragmentation device: (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of (i) a quadrupole mass filter (ii) a 2D or linear quadrupole ion trap, (iii) a Paul or 3D quadrupole ion trap, (iv) a Penning ion trap; (v) an ion trap; (vi) a magnetic sector mass filter; (vii) a Time of Flight mass filter, and (viii) a Wein filter; and/or (k) a device or ion gate for pulsing ions; and/or (l) a device for converting a substantially continuous ion beam into a pulsed ion beam The mass spectrometer preferably further comprises either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The ion mobility spectrometer according to the preferred embodiment may comprise a plurality of electrodes each having an aperture through which ions are transmitted in use. One or more transient DC voltages or potentials or one or more DC voltage or potential waveforms are preferably applied to the electrodes comprising the ion mobility spectrometer in order to urge ions along the length of the ion mobility spectrometer.

According to the preferred embodiment the one or more transient DC voltages or potentials or the one or more DC voltage or potential waveforms create: (i) a potential hill or barrier; (ii) a potential well; (iii) multiple potential hills or barriers; (iv) multiple potential wells; (v) a combination of a potential hill or barrier and a potential well; or (vi) a combination of multiple potential hills or barriers and multiple potential wells.

The one or more transient DC voltage or potential waveforms preferably comprise a repeating waveform or square wave.

An RF voltage is preferably applied to the electrodes of the ion mobility spectrometer and preferably has an amplitude selected from the group consisting of: (i)<50 V peak to peak; (ii) 50-100 V peak to peak; (iii) 100-150 V peak to peak; (iv) 150-200 V peak to peak, (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; (xi) 500-550 V peak to peak; (xxii) 550-600 V peak to peak; (xxiii) 600-650 V peak to peak; (xxiv) 650-700 V peak to peak; (xxv) 700-750 V peak to peak; (xxvi) 750-800 V peak to peak; (xxvii) 800-850 V peak to peak; (xxviii) 850-900 V peak to peak; (xxix) 900-950 V peak to peak; (xxx) 950-1000 V peak to peak; and (xxxi)>1000 V peak to peak.

The RF voltage preferably have a frequency selected from the group consisting of (i)<100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv)>10.0 MHz.

The ion mobility spectrometer is preferably maintained at a pressure selected from the group comprising: (i)>0.001 mbar; (ii)>0.01 mbar; (iii)>0.1 mbar; (iv)>1 mbar; (v)>10 mbar; (vi)>100 mbar; (vii) 0.001-0.01 mbar; (viii) 0.01-0.1 mbar; (ix) 0.1-1 mbar; (x) 1-10 mbar; and (xi) 10-100 mbar.

BRIEF DESCRIPTION OF THE DRAWINGS

Various embodiments of the present invention will now be described, by way of example only, and with reference to the accompanying drawings in which:

FIG. 1A shows an ion mobility chromatogram and indicates the drift time for undeuterated $3^+$ ions of substance P which have two different conformations and hence two different drift times through an ion mobility spectrometer, FIG. 1B shows a ion mobility chromatogram of $3^+$ ions of substance P which on the basis of their isotope ratio pattern were determined to have been subjected to seven hydrogen-deuterium exchanges and wherein such ions eluted at two different times and FIG. 1C shows an ion mobility chromatogram of $3^+$ ions of substance P which on the basis of their isotope ratio pattern were determined to have been subjected to five hydrogen-deuterium exchanges and wherein the ions eluted at substantially the same time;

FIG. 2A shows a mass spectrum of undeuterated $3^+$ ions of substance P which emerged from an ion mobility spectrometer after 34 drift time units, FIG. 2B shows a corresponding mass spectrum of undeuterated $3^+$ ions of substance P which emerged from an ion mobility spectrometer after 24 drift time units, FIG. 2C shows a mass spectrum of $3^+$ ions of substance P which have been subjected to hydrogen-deuterium exchange and emerge from an ion mobility spectrometer after 24 drift time units, FIG. 2D shows a mass spectrum of 3+ ions of substance P which have been subjected to hydrogen-deuterium exchange and emerge from an ion mobility spectrometer after 34 drift time units, FIG. 2E shows a simulated mass spectrum of 3+ ions of substance P which were simulated as having been subjected to five hydrogen-deuterium exchanges and FIG. 2F shows a simulated mass spectrum of 3+ ions of substance P which were simulated as having been subjected to seven hydrogen-deuterium exchanges;

FIG. 3A shows a mass spectrum of the ions eluting from an ion mobility spectrometer as represented by peak A in FIG. 1A and shows that these ions do not form adduct ions with the deuterated ammonia ($ND_3$) and FIG. 3B shows a mass spectrum of the ions eluting from an ion mobility spectrometer as represented by peak B in FIG. 1A and shows that these ions do form adduct ions having a mass to charge ratio of 459 as a result of the substance P ions combining with deuterated ammonia ($ND_3$)

DETAILED DESCRIPTION OF THE PREFERRED EMBODIMENT

Figure 4:
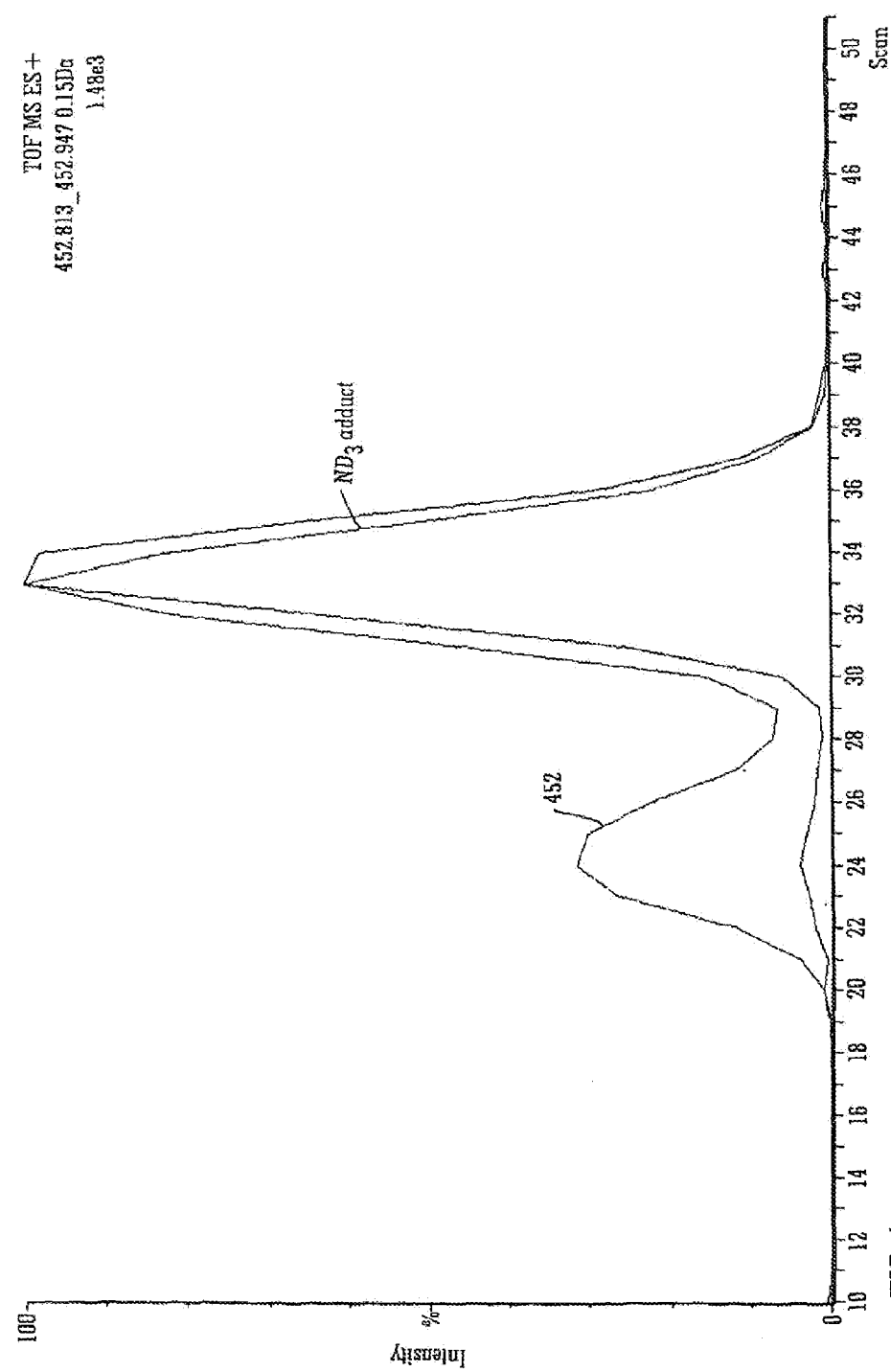
FIG. 4 shows an ion mobility chromatogram corresponding to the most intense peak shown in the mass spectra shown in FIGS. 3A and 3B which corresponds to ions having a mass to charge ratio of 452 together with an overlapping ion mobility chromatogram corresponding to the most intense peak corresponding to the adduct ions shown in FIG. 3B which have a mass to charge ratio of 459.

A preferred embodiment of the present invention will now be described. According to the preferred embodiment a mass spectrometer comprising a modified Waters Synapt® hybrid quadrupole Time of Flight mass spectrometer is provided.

The mass spectrometer comprises a first (inlet) vacuum chamber which is followed by a second vacuum chamber housing a travelling wave ion guide. Ions pass from the first vacuum chamber into the second vacuum chamber. The axis of the second vacuum chamber is preferably inclined at 90° to the axis of the first vacuum chamber.

The travelling wave ion guide arranged in the second vacuum chamber preferably comprises a plurality of ring electrodes each having an aperture through which ions are transmitted. Ions are confined radially within the travelling wave ion guide by applying opposite phases of an RF voltage to alternate electrodes thereby generating a radial pseudo-potential barrier which acts to confine ions radially within the ion guide. Ions which are transmitted through the ion guide in the second vacuum chamber are then passed to a third vacuum chamber which is located downstream of the second vacuum chamber.

The third vacuum chamber preferably houses a quadrupole rod set mass filter (MS1). In a mode of operation parent ions of interest may be selected by the quadrupole rod set mass filter MS1 and are passed onwards to a fourth vacuum chamber located downstream of the third vacuum chamber. Ions having mass to charge ratios which are not of interest are preferably filtered out or are otherwise attenuated by the mass filter MS1.

The fourth vacuum chamber downstream of the third vacuum chamber preferably comprises an ion trap gas cell, an ion mobility spectrometer ("IMS") and a transfer section.

According to the preferred embodiment analyte ions of interest are preferably selectively transmitted by the quadrupole rod set mass filter MS1 and are then preferably subjected to hydrogen-deuterium exchange CHDX") reactions within the ion trap gas cell in the fourth vacuum chamber.

Deuterated ammonia is preferably admitted into the ion trap gas cell located in the fourth vacuum chamber. As a result, analyte ions which are transmitted into the ion trap gas cell are preferably caused to be subjected to hydrogen-deuterium exchange reactions. The hydrogen-deuterium exchange reactions preferably occur on or at the surface of the analyte ions as the analyte ions pass through the ion trap gas cell.

Analyte ions which are modified by hydrogen-deuterium exchange reactions are shifted to higher masses or mass to charge ratios depending upon the surface conformation of the analyte ions and the number of sites on the surface of the analyte ion which are available for hydrogen-deuterium exchange.

Deuterated analyte ions which emerge from the ion trap gas cell are then preferably passed to the ion mobility spectrometer ("IMS") which is arranged to separate the deuterated ions on the basis of their ion mobility. The deuterated ions which emerge from the ion mobility spectrometer then preferably pass through the transfer section and are onwardly transmitted to a Time of Flight mass analyser (MS2) located in a fifth vacuum chamber arranged downstream of the fourth vacuum chamber.

According to a less preferred embodiment the ion mobility spectrometer may be arranged upstream of the ion trap gas cell and analyte ions may first be separated temporally according to their ion mobility before being subjected to hydrogen-deuterium exchange in the ion trap gas cell.

An advantageous aspect of the preferred embodiment is that if two ions have substantially similar ion mobilities then the ions can be differentiated more effectively, if they have different surface conformations, by determining the relative degree to which the ions are susceptible to hydrogen-deuterium exchange reactions.

In order to illustrate aspects of the preferred embodiment experimental data was generated using a modified Waters Synapt® hybrid quadrupole Time of Flight mass spectrometer as described above. The experimental data will be discussed in more detail below.

Substance-P was ionised by a nanospray ion source and triply charged precursor or parent ions having a mass to charge ratio of 450 were selected by the quadrupole rod set mass filter. MS1 arranged in the third vacuum chamber.

The 3+ parent ions of substance P having a mass to charge ratio of 450 which were selected by the quadrupole rod set mass filter MS1 were then passed to the ion trap gas cell located in the fourth vacuum chamber. The 3+ parent ions were then subjected to hydrogen-deuterium exchange reactions with deuterated ammonia reagent gas within the ion trap gas cell. The deuterated ammonia gas was supplied to the ion trap gas cell. The ion trap gas cell was pressurised to around $3 \times 10^{-2}$ mbar with helium. An additional gas inlet needle valve was connected to the ion trap gas cell and was used to introduce deuterated ammonia into the ion trap gas cell causing the pressure in the ion trap gas cell to increase from $3 \times 10^{-2}$ mbar to $3.5 \times 10^{-2}$ mbar.

The parent ions which had been subjected to hydrogen-deuterium exchange within the ion trap gas cell were then passed to the ion mobility spectrometer where the ions were caused to separate temporally according to their ion mobility. Ions which eluted from the ion mobility spectrometer were then mass analysed by the Time of Flight mass analyser MS2.

It was evident from measuring the ion mobility or drift times of the parent ions which had been subjected to hydrogen-deuterium exchange and which were separated according to their ion mobility by the ion mobility spectrometer that the 3+ parent ions of substance P comprise a mixture of ions having two different cross sections or conformations. Two distinct arrival time distributions are observed as eluting from the ion mobility spectrometer.

FIG. 1A shows an ion mobility chromatogram of undeuterated 3+ parent ions of substance P which emerge from the ion mobility spectrometer. Two distinct peaks (peak A and peak B) are observed in the ion mobility chromatogram suggesting that the parent ions of substance P comprise two different conformations. According to the preferred embodiment this assumption can be tested further so that a greater degree of certainty is obtained. Furthermore, further information relating to differences between the two different conformations can be obtained as will be discussed below.

FIG. 1B shows an ion mobility chromatogram of 3+ ions of substance P which on the basis of their isotope ratio pattern from mass spectral data were determined as having been subjected to seven hydrogen-deuterium exchanges. The ion mobility chromatogram indicates that such ions elute from the ion mobility spectrometer at two different times (i.e. after 24 and 34 drift time units).

FIG. 1C shows an ion mobility chromatogram of 3+ ions of substance P which on the basis of their isotope ratio pattern from mass spectral data were determined as having been subjected to five hydrogen-deuterium exchanges and which indicates that such ions elute substantially at the same time (i.e. after 34 drift time units).

Admitting deuterated ammonia ($ND_3$) into the ion trap gas cell of the mass spectrometer enabled hydrogen atoms in or on the exposed surface of the 3+ parent ions of substance P to be exchanged for deuterium.

FIG. 2A shows a mass spectrum of undeuterated 3+ ions of substance P which emerge from the ion mobility spectrometer after 34 drift time units and FIG. 2B shows a corresponding mass spectrum of undeuterated 3+ ions of substance P which emerge from the ion mobility spectrometer after 24 drift time units.

FIGS. 2A and 2B suggest that undeuterated 3+ parent ions of substance P have two different conformations which have two different drift times through the ion mobility spectrometer.

FIGS. 2C and 2D show corresponding mass spectra obtained after 3+ parent ions of substance P were subjected to hydrogen-deuterium exchange with deuterated ammonia in the ion trap gas cell. FIG. 2C shows a mass spectrum which was obtained relating to ions which emerged from the ion mobility spectrometer after 24 drift time units and FIG. 2D shows a mass spectrum which was obtained relating to ions which emerged from the ion mobility spectrometer after 34 drift time units.

It can be seen from comparing FIGS. 2C and 2D with FIGS. 2A and 2B that hydrogen-deuterium exchange causes there to be a shift in the mass spectrum to higher mass to charge ratios. It will also be apparent that the isotope ratio pattern of the mass spectrum shown in FIG. 2C is different from the isotope ratio pattern of the mass spectrum shown in FIG. 2D.

As will be discussed in more detail below, FIG. 2D also shows the presence of adduct ions having a mass to charge ratio of 459. Adduct ions are not observed in FIG. 2C.

FIG. 2E shows a simulated mass spectrum which is predicted to be observed if 3+ parent ions of substance P are subjected to five hydrogen-deuterium exchange reactions. FIG. 2F shows a simulated mass spectrum which is predicted to be observed if 3+ parent ions of substance P are subjected to seven hydrogen-deuterium exchange reactions.

When deuterated ammonia was added to the ion trap gas cell, the mass to charge ratio of the analyte ions which were subjected to hydrogen-deuterium exchange were observed to increase. The deuterated ions were separated according to their ion mobility in the ion mobility spectrometer and mass spectra of the deuterated ions eluting from the ion mobility spectrometer were obtained and analysed. In particular, the isotope pattern of the deuterated ions in a resulting mass spectrum were deconvoluted to determine the relative exchange for the different sites of deuteration exposed on the surface of the analyte ions. According to the preferred embodiment deconvolution of the isotope pattern can be used to determine the number of surface sites for hydrogen-deuterium exchange which the ions possess.

It is evident from comparing FIG. 2C with FIG. 2F and from analysing and comparing the isotope ratio patterns that the more compact isomer 3+ ions of substance-P which emerge from the ion mobility spectrometer after 24 drift time units possess approximately seven sites for hydrogen-deuterium exchange. Similarly, from comparing FIG. 2O with FIGS. 2E and 2F then the more unfolded isomer 3+ ions of substance-P which emerges from the ion mobility spectrometer after 34 drift time units comprises ions having a mixture of seven active hydrogen-deuterium exchange sites and five active hydrogen-deuterium exchange sites.

FIG. 3A shows a mass spectrum of the ions constituting peak A shown in FIG. 1A and shows that these ions do not form adduct ions with the deuterated ammonia ($ND_3$) in the ion trap gas cell. FIG. 3B shows a mass spectrum of the ions constituting peak shown in FIG. 1A and shows that these ions form adduct ions i.e. some ions are formed by substance P ions combining with deuterated ammonia ($ND_3$). The ions constituting peak B shown in FIG. 1A are relatively unfolded and have a longer drift time of 34 drift time units and comprise ions having a mixture of five and seven hydrogen-deuterium exchange sites. It will be apparent that whether or not ions form adduct ions with deuterated ammonia ($ND_3$) can be used as a further way of differentiating between two ions having substantially similar ion mobility drift times.

FIG. 4 shows an ion mobility chromatogram related to the most intense peak shown in FIGS. 3A and 3B which corresponds to ions having a mass to charge ratio of 452 together with an overlapping ion mobility chromatogram related to the most intense peak which corresponds with the adduct ions shown in FIG. 3B and which have a mass to charge ratio of 459.

The data shown in FIG. 4 indicates that the less compact conformation of substance-P which has the greater ion mobility drift time of 34 drift time units also reacts directly with deuterated ammonia ($ND_3$) to form stable deuterated ammonium adduct ions. However, the more compact conformation of substance-P ions which have a shorter ion mobility drift time of 24 drift time units hardly react at all with the deuterated ammonia and hence the intensity of adduct ions which emerge after 24 drift time units is relatively very low.

By plotting ion mobility drift time chromatograms of isotopes associated with specific hydrogen-deuterium exchange shifts the differing signal profiles enable the differentiation of isomeric species with very similar cross sections.

Furthermore, plotting an ion mobility chromatogram for deuterated substance-P having a mass to charge ratio of 452 and overlapping an ion mobility chromatogram relating to deuterated adduct ions (FIG. 4) enables clear differentiation between the two isomeric conformations in that ions having a mass to charge ratio of 452 which elute after 24 drift time units substantially do not form adduct ions with the deuterated ammonia whereas ions having a mass to charge ratio of 452 which elute after 34 drift time units do form adduct ions with the deuterated ammonia.

Although the experimental data presented above relates to substance-P where it is possible to observe differing ion mobility separator peaks without requiring hydrogen-deuterium exchange, isomeric ions having different conformations and almost identical ion mobility drift times can be deconvoluted and more accurately determined according to the preferred embodiment of the present invention.

Although the present invention has been described with reference to the preferred embodiment, it will be understood by those skilled in the art that various changes in form and detail may be made without departing from the scope of the invention as set forth in the accompanying claims.

The invention claimed is:

1. A method of mass spectrometry comprising:
    subjecting first and second analyte ions to hydrogen-deuterium exchange within a first device wherein one or more hydrogen atoms of said first and second analyte ions exchange with one or more deuterium atoms to form first and second deuterated ions;
    passing said first and second deuterated ions from said first device to an ion mobility spectrometer and temporally separating said first and second deuterated ions within said ion mobility spectrometer according to their ion mobility;
    mass analysing deuterated ions which emerge from said ion mobility spectrometer at a first time to produce first mass spectral data;
    mass analysing deuterated ions which emerge from said ion mobility spectrometer at a second later time to produce second mass spectral data; and
    comparing said first mass spectral data with said second mass spectral data using a control system to aid differentiation between either: (i) said first and second analyte ions; or (ii) said first deuterated ions and said second deuterated ions.

2. A method of mass spectrometry comprising:
    passing first and second analyte ions to an ion mobility spectrometer and temporally separating said first and second analyte ions within said ion mobility spectrometer according to their ion mobility;
    subjecting said first and second analyte ions which emerge from said ion mobility spectrometer to hydrogen-deuterium exchange within a first device wherein one or more hydrogen atoms of said first and second analyte ions exchange with one or more deuterium atoms to form first and second deuterated ions;
    mass analysing deuterated ions which emerge from said first device at a first time to produce first mass spectral data;
    mass analysing deuterated ions which emerge from said first device at a second later time to produce second mass spectral data; and
    comparing said first mass spectral data with said second mass spectral data using a control system to aid differentiation between either: (i) said first and second analyte ions; or (ii) said first deuterated ions and said second deuterated ions.

3. A method as claimed in claim 1, wherein said step of comparing said first mass spectral data with said second mass spectral data to aid differentiation comprises determining differences in structural or conformational properties or reactiveness with a gas in said first device between either: (i) said first and second analyte ions; or (ii) said first deuterated ions and said second deuterated ions.

4. A method as claimed in claim 1, wherein said step of comparing said first mass spectral data with said second mass spectral data comprises:
    (i) determining or approximating the degree to which hydrogen atoms in said first or second analyte ions are exchanged for deuterium atoms;
    (ii) determining or approximating structural or conformational properties of said first or second analyte ions;
    (iii) determining or approximating structural or conformational properties of said first or second deuterated ions;
    (iv) determining or approximating the relative compactness or elongation of said first or second analyte ions;
    (v) determining or approximating the relative compactness or elongation of said first or second deuterated ions;
    (vi) determining or approximating the degree to which said first and/or second analyte ions react with said gas in said first device to form adduct ions
    (vii) determining or approximating the number of surface sites on said first or second analyte ions at which hydrogen atoms may exchange for deuterium atoms; or
    (viii) comparing one or more isotope patterns or one or more isotope distributions or one or more isotope ratios related to said first deuterated ions with one or more isotope patterns or one or more isotope distributions or one or more isotope ratios related to said second deuterated ions.

5. A method of mass spectrometry as claimed in claim 1, further comprising providing a mass filter upstream of said ion mobility spectrometer or said first device, and operating said mass filter to selectively transmit said first and second analyte ions having substantially the same mass to charge ratio and to filter out or attenuate other ions having different mass to charge ratios.

6. A mass spectrometer comprising:
    a first device arranged and adapted to subject first and second analyte ions to hydrogen-deuterium exchange wherein one or more hydrogen atoms of said first and second analyte ions exchange with one or more deuterium atoms to form first and second deuterated ions;
    an ion mobility spectrometer, wherein said first and second deuterated ions are passed, in use, from said first device to said ion mobility spectrometer and are temporally separated within said ion mobility spectrometer according to their ion mobility;
    a mass analyser arranged and adapted to mass analyse deuterated ions which emerge from said ion mobility spectrometer at a first time to produce first mass spectral data; and to mass analyse deuterated ions which emerge from said ion mobility spectrometer at a second later time to produce second mass spectral data; and
    a control system arranged and adapted to compare said first mass spectral data with said second mass spectral data to aid differentiation between either: (i) said first and second analyte ions; or (ii) said first deuterated ions and said second deuterated ions.

7. A mass spectrometer comprising:
    an ion mobility spectrometer, wherein first and second analyte ions are passed to said ion mobility spectrometer and are temporally separated within said ion mobility spectrometer according to their ion mobility;
    a first device arranged and adapted to subject said first and second analyte ions which emerge from said ion mobility spectrometer to hydrogen-deuterium exchange within said first device wherein one or more hydrogen atoms of said first and second analyte ions exchange with one or more deuterium atoms to form first and second deuterated ions;
    a mass analyser arranged and adapted to mass analyse deuterated ions which emerge from said first device at a first time to produce first mass spectral data and to mass analyse deuterated ions which emerge from said first device at a second later time to produce second mass spectral data; and a control system arranged and adapted to compare said first mass spectral data with said second mass spectral data to aid differentiation between either: (i) said first and second analyte ions; or (ii) said first deuterated ions and said second deuterated ions.

8. A mass spectrometer as claimed in claim 6, wherein said control system is arranged and adapted to determine differences in structural or conformational properties or reactiveness with a gas in said first device between either:
(i) said first and second analyte ions; or (ii) said first deuterated ions and said second deuterated ions.

9. A mass spectrometer as claimed in claim 6, wherein said control system is arranged and adapted to:
(i) determine or approximate the degree to which hydrogen atoms in said first or second analyte ions are exchanged for deuterium atoms;
(ii) determine or approximate structural or conformational properties of said first or second analyte ions;
(iii) determine or approximate structural or conformational properties of said first or second deuterated ions;
(iv) determine or approximate the relative compactness or elongation of said first or second analyte ions;
(v) determine or approximate the relative compactness or elongation of said first or second deuterated ions;
(vi) determine or approximate the degree to which said first or second analyte ions react with said gas in said first device to form adduct ions;
(vii) determine or approximate the number of surface sites on said first or second analyte ions at which hydrogen atoms may exchange for deuterium atoms; or
(viii) compare one or more isotope patterns or one or more isotope distributions or one or more isotope ratios related to said first deuterated ions with one or more isotope patterns or one or more isotope distributions or one or more isotope ratios related to said second deuterated ions.

10. A mass spectrometer as claimed in claim 6, wherein said mass analyser comprises a Time of Flight mass analyser.

11. A mass spectrometer as claimed in claim 6, further comprising a mass filter arranged upstream of said ion mobility spectrometer or said first device, wherein in a mode of operation said mass filter is arranged and adapted to selectively transmit said first and second analyte ions having substantially the same mass to charge ratio and to filter out or attenuate other ions having different mass to charge ratios.

12. A method of mass spectrometry comprising:
subjecting analyte ions to hydrogen-deuterium exchange within a first device wherein one or more hydrogen atoms of said analyte ions exchange with one or more deuterium atoms to form deuterated ions;
passing said deuterated ions from said first device to an ion mobility spectrometer and temporally separating said deuterated ions within said ion mobility spectrometer according to their ion mobility;
mass analysing, using a mass analyzer, first deuterated ions which emerge from said ion mobility spectrometer at a first time to produce first mass spectral data;
deconvoluting, using a control system, one or more isotope ratio patterns in said first mass spectral data to determine or approximate the number of hydrogen atoms which have been exchanged for deuterium atoms in said first deuterated ions;
mass analysing, using a mass analyzer, second deuterated ions which emerge from said ion mobility spectrometer at a second later time to produce second mass spectral data; and
deconvoluting, using a control system, one or more isotope ratio patterns in said second mass spectral data to determine or approximate the number of hydrogen atoms which have been exchanged for deuterium atoms in said second deuterated ions.

13. A mass spectrometer comprising:
a first device arranged and adapted to subject analyte ions to hydrogen-deuterium exchange wherein one or more hydrogen atoms of said analyte ions exchange with one or more deuterium atoms to form deuterated ions;
an ion mobility spectrometer, wherein said deuterated ions are passed, in use, from said first device to said ion mobility spectrometer and are temporally separated within said ion mobility spectrometer according to their ion mobility;
a control system and mass analyser arranged and adapted:
(i) to mass analyse first deuterated ions which emerge from said ion mobility spectrometer at a first time to produce first mass spectral data;
(ii) to deconvolute one or more isotope ratio patterns in said first mass spectral data to determine or approximate the number of hydrogen atoms which have been exchanged for deuterium atoms in said first deuterated ions;
(iii) to mass analyse second deuterated ions which emerge from said ion mobility spectrometer at a second later time to produce second mass spectral data; and
(iv) to deconvolute one or more isotope ratio patterns in said second mass spectral data to determine or approximate the number of hydrogen atoms which have been exchanged for deuterium atoms in said second deuterated ions.

* * * * *